US009585806B2

(12) United States Patent
Herrig (10) Patent No.: US 9,585,806 B2
(45) Date of Patent: Mar. 7, 2017

(54) VARIABLE RATE BEDRAIL CLAMP

(71) Applicant: ACIST Medical Systems, Inc., Eden Prairie, MN (US)

(72) Inventor: Judson A. Herrig, Elko New Market, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 0 days.

(21) Appl. No.: 14/736,464

(22) Filed: Jun. 11, 2015

(65) Prior Publication Data

US 2016/0361219 A1    Dec. 15, 2016

(51) Int. Cl.
*F16B 2/12* (2006.01)
*A61G 13/10* (2006.01)
*A61B 19/00* (2006.01)
*F16B 2/14* (2006.01)

(52) U.S. Cl.
CPC ............ *A61G 13/101* (2013.01); *A61B 19/26* (2013.01); *F16B 2/12* (2013.01); *F16B 2/14* (2013.01); *A61B 2019/268* (2013.01)

(58) Field of Classification Search
USPC ..... 269/2, 86, 89, 90, 87, 98, 104, 110, 112, 269/113, 118, 122, 132, 134, 136, 137, 269/138, 139, 142, 217, 218, 220, 229, 269/234, 258; 248/227.2, 227.4, 228.2, 248/228.3, 228.5, 228.6, 231.31, 231.41, 248/231.61, 316.2, 316.4, 316.6
See application file for complete search history.

(56) References Cited

U.S. PATENT DOCUMENTS

| | | | |
|---|---|---|---|
| 200,082 A | 2/1878 | Nolan | |
| 602,055 A | 4/1898 | Campbell | |
| 1,033,531 A | 7/1912 | Brown | |
| 2,437,267 A * | 3/1948 | Mayrath | ................ B25B 13/16 269/137 |
| 2,543,017 A | 2/1951 | Hagan | |
| 2,564,138 A * | 8/1951 | Walker | ..................... B25B 1/24 269/138 |
| 2,915,096 A | 12/1959 | Mooney | |
| 3,331,111 A | 7/1967 | Leonard | |

(Continued)

FOREIGN PATENT DOCUMENTS

CN    201140784 Y    10/2008
DE    29920169 U1    2/2000

(Continued)

OTHER PUBLICATIONS

International Search Report & Written Opinion mailed Jan. 17, 2012, in PCT Application No. PCT/US2011/058219, 13 pages.

(Continued)

*Primary Examiner* — Alfred J Wujciak
(74) *Attorney, Agent, or Firm* — Fredrikson & Byron, P.A.

(57) ABSTRACT

A bedrail clamp with a jaw member positionable by an actuating member, the actuating member being configured to move to move the jaw member away from the bedrail and toward the bedrail to move the jaw member into contact with the bedrail to secure the bedrail against the clamp housing. Either the actuating member or the jaw member features an inclined surface that includes a first portion with a first angle and a second portion with a second angle. Methods of operating a bedrail clamp.

18 Claims, 6 Drawing Sheets

(56) References Cited

U.S. PATENT DOCUMENTS

| | | | |
|---|---|---|---|
| 3,612,462 A * | 10/1971 | Mooney | F16M 11/04 |
| | | | 248/187.1 |
| 4,511,158 A | 4/1985 | Varga et al. | |
| 4,705,331 A | 11/1987 | Britton | |
| 4,898,371 A * | 2/1990 | Mills | B25B 1/103 |
| | | | 269/136 |
| 4,901,964 A | 2/1990 | McConnell | |
| 5,146,816 A | 9/1992 | Badstieber | |
| 5,306,109 A | 4/1994 | Kreuzer et al. | |
| 5,398,901 A | 3/1995 | Brodmann et al. | |
| 6,499,158 B1 | 12/2002 | Easterling | |
| 6,585,206 B2 | 7/2003 | Metz et al. | |
| 7,065,811 B2 | 6/2006 | Newkirk et al. | |
| 7,418,749 B2 | 9/2008 | Graham et al. | |
| 7,520,007 B2 | 4/2009 | Skripps | |
| 7,676,865 B2 | 3/2010 | Graham et al. | |
| 7,703,358 B2 | 4/2010 | Felix | |
| 7,966,703 B2 | 6/2011 | Felix | |
| 8,104,729 B2 | 1/2012 | Walke et al. | |
| 8,585,000 B2 * | 11/2013 | McpPheeters | E04D 13/1476 |
| | | | 248/228.2 |
| 2002/0047075 A1 | 4/2002 | Metz et al. | |
| 2006/0242763 A1 | 11/2006 | Graham et al. | |
| 2006/0290076 A1 | 12/2006 | Lees | |
| 2007/0138354 A1 | 6/2007 | Graham et al. | |
| 2008/0217910 A1 | 9/2008 | Walke et al. | |
| 2010/0024176 A1 | 2/2010 | Ubinana Felix et al. | |
| 2010/0108841 A1 | 5/2010 | Kronner et al. | |
| 2012/0126079 A1 | 5/2012 | Russell | |
| 2013/0182381 A1 * | 7/2013 | Gray | F16M 13/02 |
| | | | 361/679.01 |

FOREIGN PATENT DOCUMENTS

| | | |
|---|---|---|
| JP | H05-507873 A | 11/1993 |
| JP | H07-500275 A | 1/1995 |
| JP | 2003159617 A | 6/2003 |
| JP | 2008501373 A | 1/2008 |
| JP | 2008539902 A | 11/2008 |
| WO | 2005037163 A2 | 4/2005 |
| WO | 2005037165 A2 | 4/2005 |
| WO | 2008111974 A1 | 9/2008 |
| WO | 2010054836 A2 | 5/2010 |

OTHER PUBLICATIONS

ACIST Contrast Delivery System User Manual for ACIST/CVi™ and CL100H, CMS2000, and Voyager™, ACIST Medical Systems, Inc., P/N 900420-001, Rev. 02, 2005, pp. 12-15.

International Patent Application No. PCT/US2016/034044, International Search Report & Written Opinion mailed Aug. 10, 2016, 12 pages.

* cited by examiner

VARIABLE RATE BEDRAIL CLAMP

TECHNICAL FIELD

The present application relates generally to attaching medical accessories to a bedrail of a surgical/medical bed.

BACKGROUND

Surgical (or related medical) procedures typically require several instruments, monitors, and other accessories. Examples of such accessories include surgical tray tables, holders for various sensors and other equipment, a contrast media injector, and so on. For many such accessories, where they are positioned in the operating room can have a significant impact on how effectively they function. Additionally, many accessories must be repositioned multiple times during the course of a surgical/medical procedure.

In many instances, it is desirable (if not required) to attach a medical accessory to a bedrail of the surgical/medical bed. For example, some sensors must be kept at a specific height relative to part of a patient's anatomy (e.g., at the same level as the midline of the patient's heart). In such instances, attaching the accessory to the bedrail of the surgical/medical bed ensures that the position of the accessory relative to that of the relevant part of the patient's anatomy remains unchanged even as the surgical/medical bed is raised and lowered during the procedure.

Bedrail clamps for attaching accessories to the bedrail have been developed, but most of them have been configured to engage the end of the bedrail and then be slid into the desired position. While such bedrail clamps may be useful in some situations, in many situations, they present significant drawbacks. A common problem with such bedrail clamps arises when multiple accessories must be attached to the bedrail in a surgical/medical procedure. For example, when two such bedrail clamps are already positioned on a bedrail, and a third bedrail clamp must be positioned between the first two, moving the third bedrail clamp into position can be quite challenging. One of the first two bedrail clamps must first be removed by being slid to the end of the bedrail and removed. Then the third bedrail clamp must be slid from the end of the bedrail back to the desired position, and the previously attached bedrail clamp must be repositioned to its original location. This problem is only enhanced when more accessories must be attached to the same bedrail. Further, clamps that can attach to the side of a bedrail can be slow and cumbersome because of the large clearance needed to initially position the clamp on the bedrail, which then must be must be traversed as the clamp is secured to the bedrail.

SUMMARY

Embodiments of the present invention provide a bedrail clamp with one or more jaw members positionable by an actuating member, the actuating member being configured to move the jaw member into contact with the bedrail to secure the bedrail against the clamp housing. Either the actuating member or the jaw member has an inclined surface with a dual-stage incline that includes a first portion with a high incline that initially allows for rapid advancement with low mechanical advantage to take up clearance between the clamp and the bedrail, followed by a second portion of low incline and higher mechanical advantage that allows for secure attachment of the clamp to the bedrail. Accordingly, embodiments of the invention allow a rail clamp to have a secure attachment with reduced user effort while minimizing the installation time.

The details of one or more examples are set forth in the accompanying drawings and the description below. Other features, objects, and advantages will be apparent from the description and drawings, and from the claims.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1:
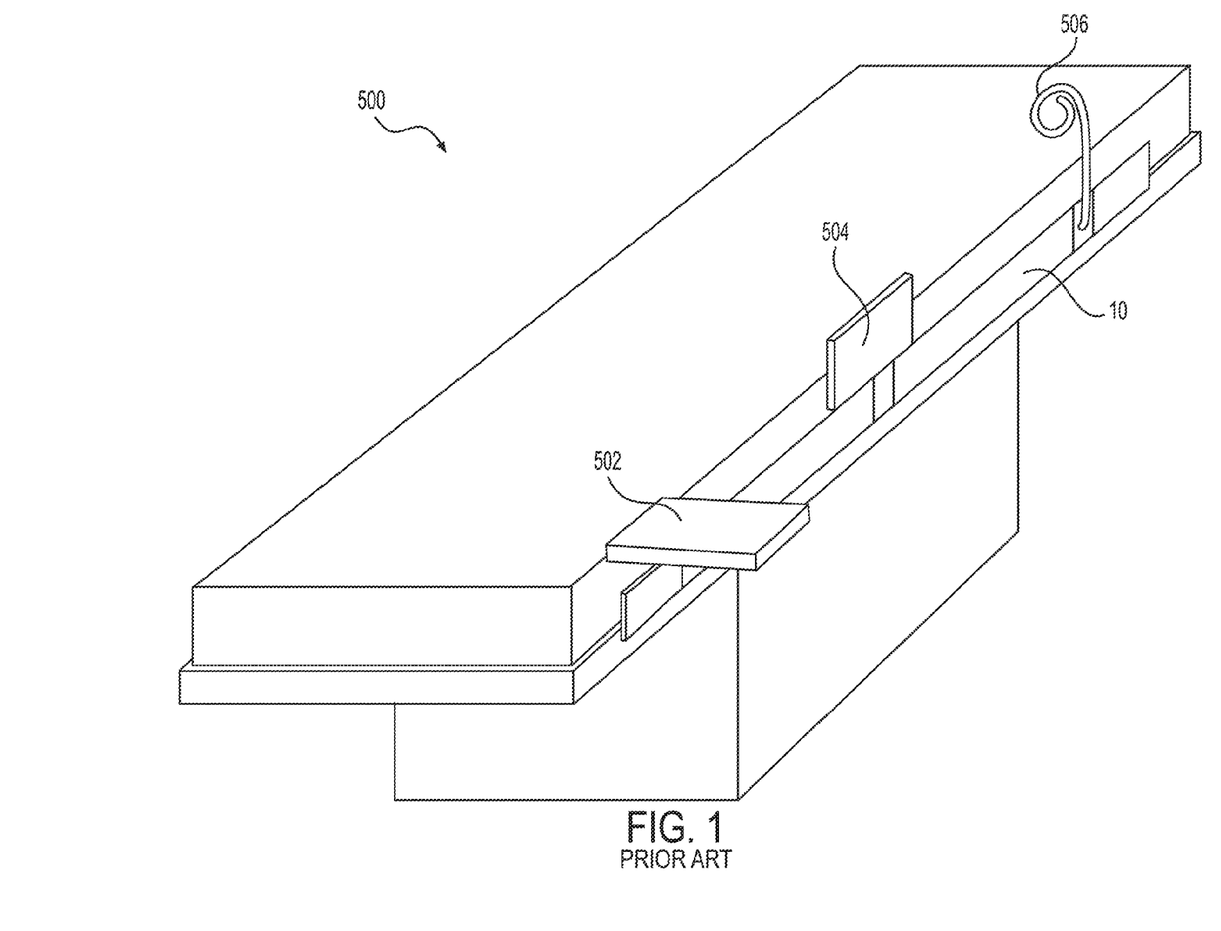
FIG. 1 is a perspective view of an illustrative operating room with a surgical/medical bed having a bedrail.

FIG. 1 shows an illustrative operating room with a surgical/medical bed 500 having a bedrail 10 to which various accessories (tray table 502, monitor 504, and holder 506) are attached. As can be seen, if only conventional end-loading bedrail clamps were available, and if an additional accessory needed to be positioned between monitor 504 and holder 506, holder 506 would first have to be slid to the end of the bedrail 10 and removed. Only then could the additional accessory be positioned between monitor 504 and holder 506. And after that, holder 506 would have to be engaged to the end 508 of the bedrail 10 and slid back into position. A similar situation would arise if monitor 504 needed to be repositioned to the other side of tray table 502. In that situation, both tray table 502 and monitor 504 must be slid to the end 510 of bedrail 10 and removed and then their positions reversed. Further, if such accessories are supported by traditional side-loading clamps, attaching such accessories to the bedrail takes valuable time because the clearance needed to initially position the clamp on the bedrail must be traversed before the clamp can be secured to the bedrail.

Embodiments of the present invention allow quick positioning and repositioning of accessories at any open position along the bedrail 10 without changing the position of any accessories that are already attached to the bedrail 10. In the examples discussed above, if an additional accessory needed to be positioned between monitor 504 and holder 506, it could simply be quickly attached in that position without even addressing the position of monitor 504 and holder 506. Likewise, if monitor 504 needed to be repositioned to the other side of tray table 502, monitor 504 could simply be quickly removed from its current position and attached on the other side of tray table 502.

FIGS. 2-5 show a bedrail clamp 5 according to embodiments of the present invention. The bedrail clamp 5 can quickly attach an accessory to a bedrail 10 of a surgical/medical bed at a desired location without having to slide the bedrail clamp 5 from an end of the bedrail 10 until the accessory is in the desired location. The bedrail clamp 5 of FIGS. 2-5 includes a clamp housing 15, an actuating member 20 housed within the clamp housing 15, and a jaw member 25 in apposition to the actuating member 20 and housed by the clamp housing 15.

As its name suggests, the clamp housing 15 can house other components of the bedrail clamp 5. In many embodiments, the clamp housing 15 is generally C-shaped and includes a throat area 30. When the bedrail clamp 5 is to be attached to the bedrail 10, the throat area 30 can receive the bedrail 10, and then the bedrail clamp 5 can be closed (as is discussed in greater detail below). The throat area 30 of the clamp housing 15 shown includes three bedrail surfaces 35, 36, 37.

Figure 3:
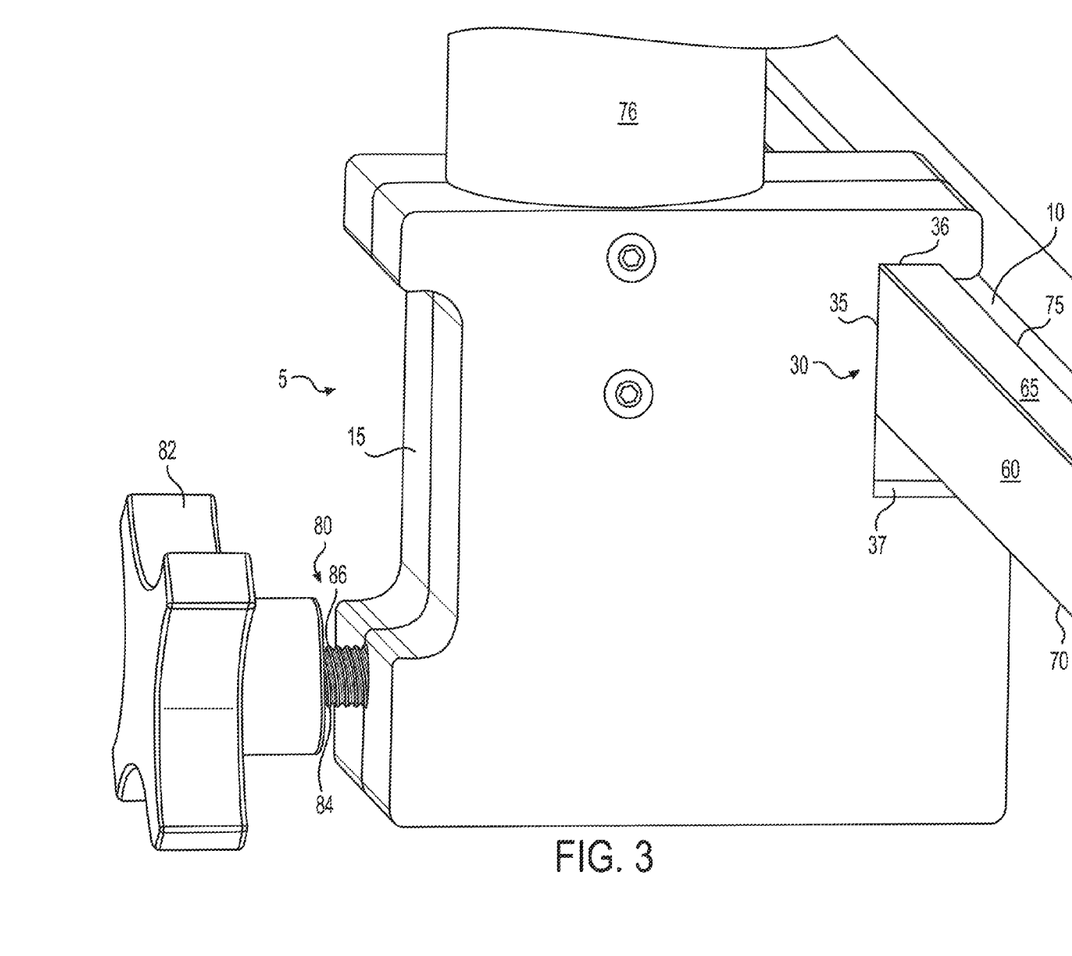
FIG. 3 is a perspective view of a bedrail clamp in accordance with an embodiment of the invention in a closed position.
Figure 4:
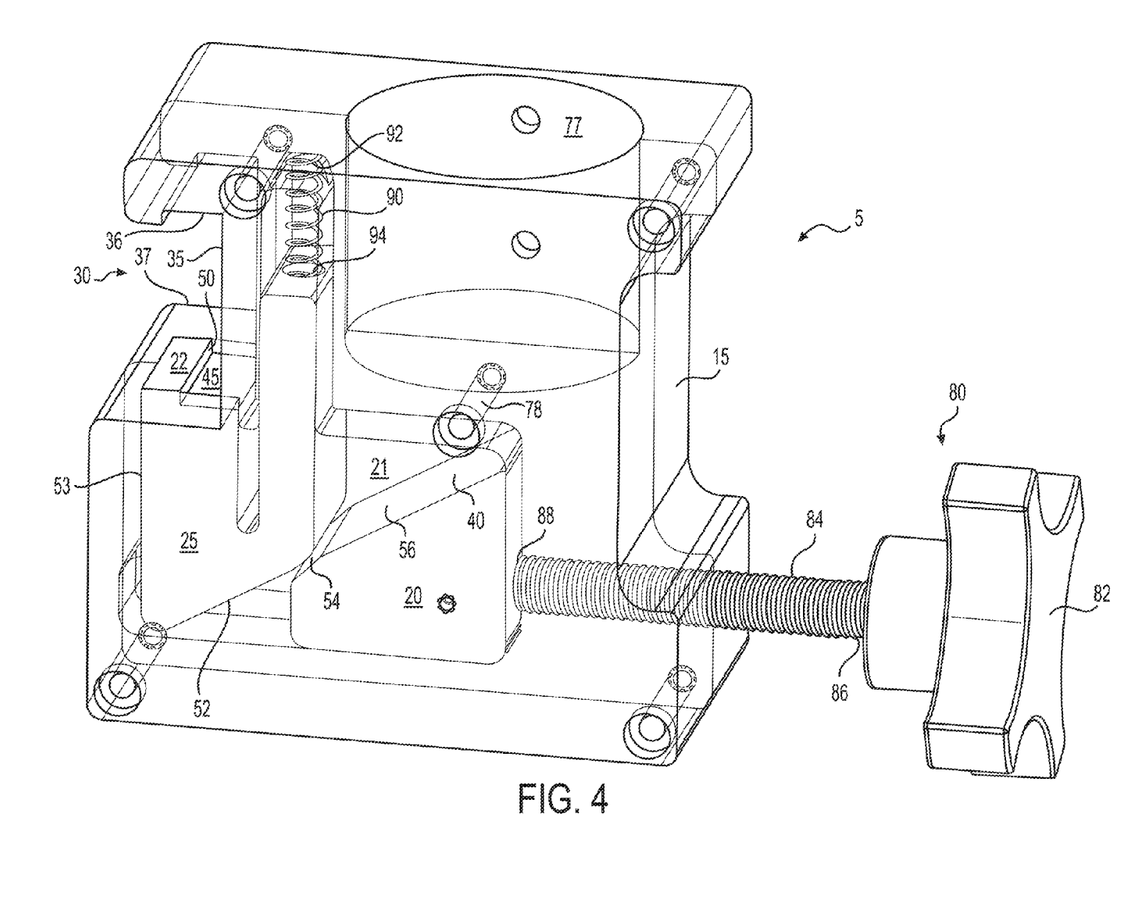
FIG. 4 is a perspective view of a bedrail clamp in accordance with an embodiment of the invention in an open position with some components depicted as transparent.
Figure 5:
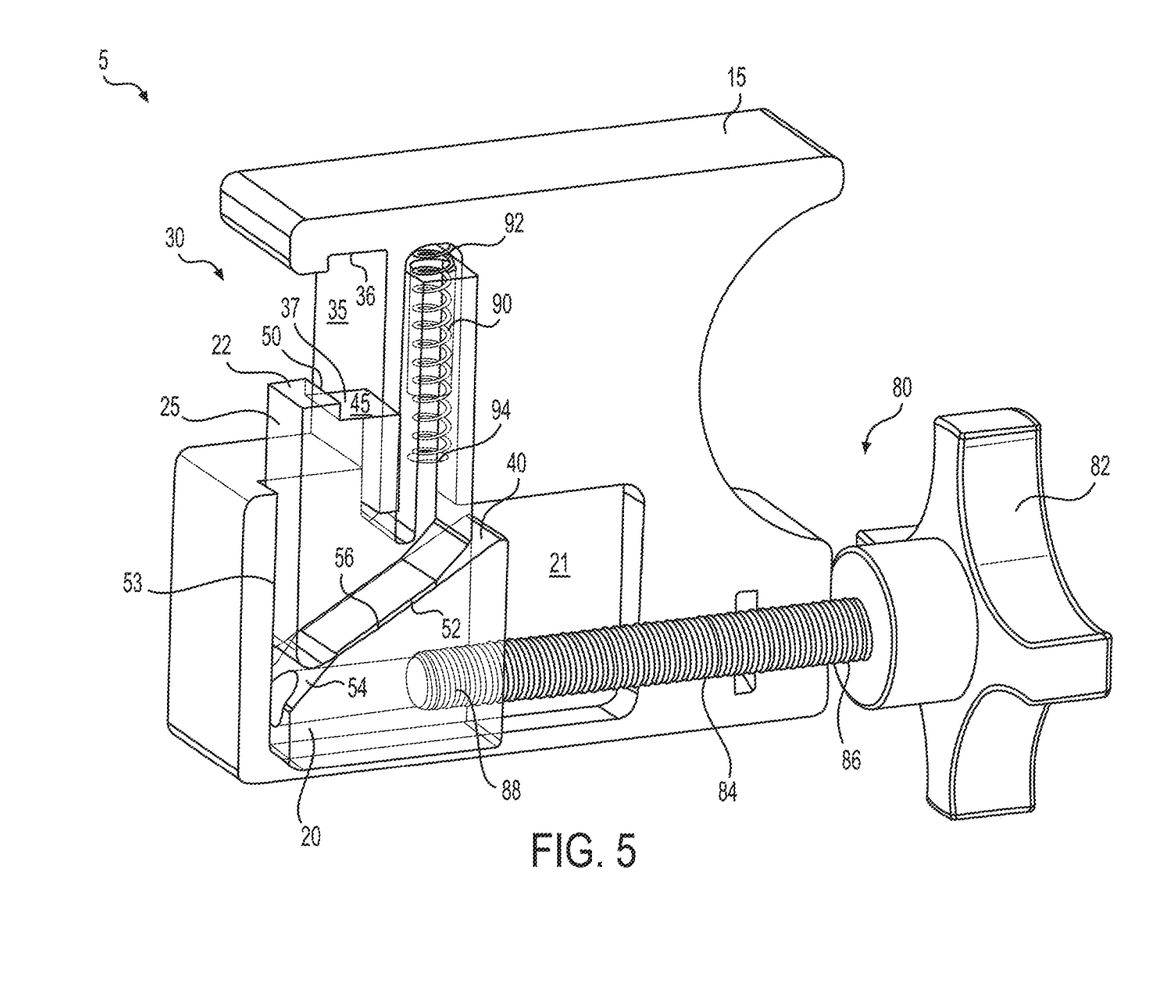
FIG. 5 is a perspective view of a bedrail clamp in accordance with an embodiment of the invention in a closed position with some components depicted as transparent.

The actuating member 20 of the bedrail clamp 5 can coordinate the opening and closing of the bedrail clamp 5. The actuating member 20 can be configured to move relative to the clamp housing 15 between a clamp-open position (FIGS. 2 and 4) and a clamp-closed position (FIGS. 3 and 5). As shown in FIGS. 4 and 5, the actuating member can move in a generally horizontal direction within a horizontal slot 21 defined by the clamp housing. When the bedrail 10 is in the clamp housing's throat area 30, the actuating member 20 can be nearer to the bedrail 10 in the clamp-closed position than in the clamp-open position. Accordingly, to go from the clamp-open position to the clamp-closed position, the actuating member 20 moves in a closing direction, and, to go from the clamp-closed position to the clamp-open position, the actuating member 20 moves in an opposite opening direction. As shown, the actuating member can include an angled surface 40 positioned at an angle with respect to a horizontal plane.

The jaw member 25 of the bedrail clamp 5 can move between a jaw-open position and a jaw-closed position based on the movement of the actuating member 20. The relative positions of the jaw-open position and the jaw-closed position will depend on the particular height of the bedrail to which the clamp will be attached. The jaw member 25 includes bedrail portions 45, 50 that are configured to interact with the bedrail 10 when in use. As shown, bedrail portion 45 has a first surface, and bedrail portion 50 has a second surface that is generally perpendicular to the first surface. Bedrail portion 45 can be configured to be positioned proximate to the bedrail 10 (i.e., contacting the bedrail 10 or positioned near the bedrail 10 without contacting it) when the jaw member 25 is in the jaw-open position. Bedrail portion 50 can be configured to engage the bedrail 10 when the jaw member 25 is in the jaw-closed position. In some embodiments, the jaw member can also include a surface 52 configured to interface physically with the actuating member's angled surface 40 as the actuating member 20 moves in a closing direction from the clamp-open position to the clamp-closed position to reposition the jaw member 25 from a jaw-open position in which the jaw member does not obstruct the bedrail from entering or exiting the clamp housing's throat area to a jaw-closed position in which, when the bedrail is in the clamp housing's throat area, the jaw member's first bedrail portion engages a surface of the bedrail. As shown, such a surface 52 can also be angled relative to horizontal. As the actuating member 20 is moved horizontally, the angle of the surfaces 40, 52 drive the jaw member 25 vertically within a vertical channel 53 defined by the clamp housing to engage a bedrail.

Figure 6:
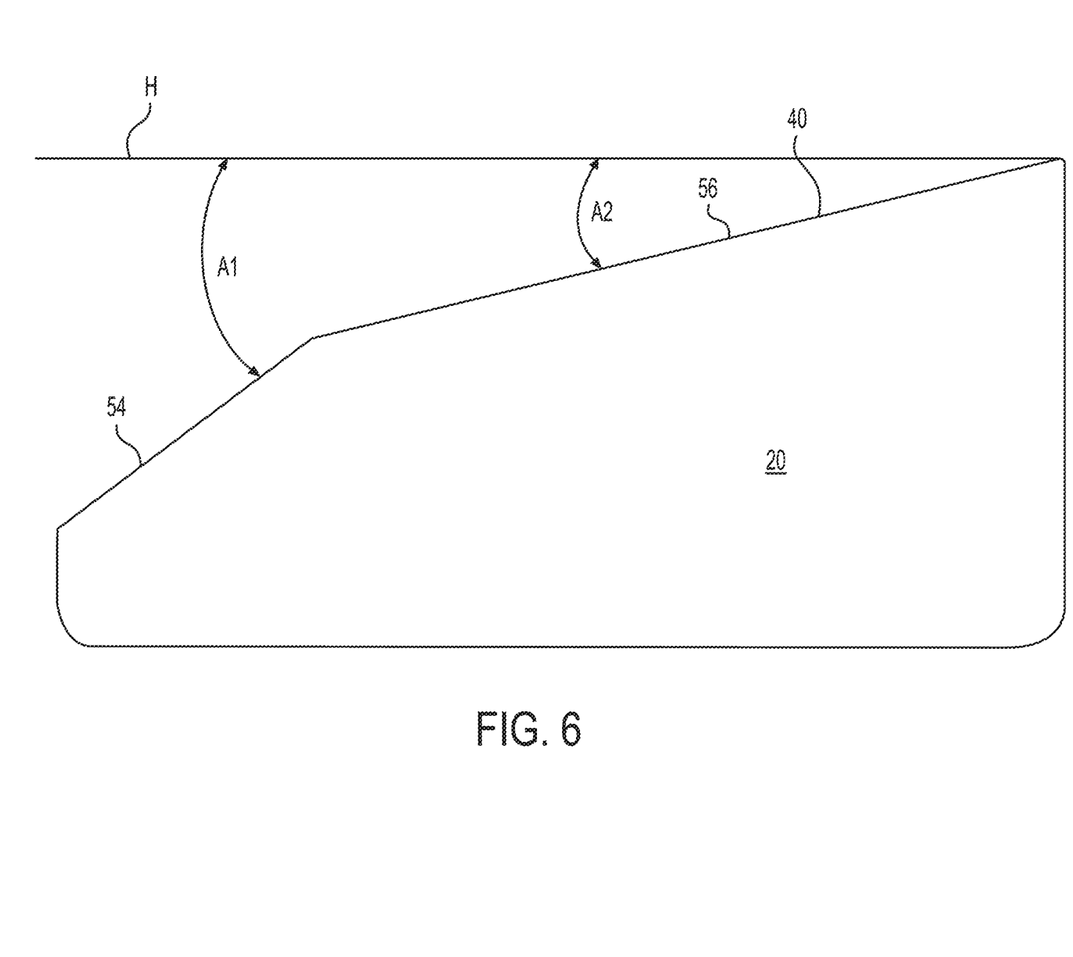
FIG. 6 is a side schematic view of an actuating member in accordance with an embodiment of the invention.

As shown in FIGS. 4-5, in some embodiments, the angled surface 40 of the actuating member 20 and/or the surface 52 configured to interface physically with the actuating member's angled surface includes a first portion 54 having a first angle with respect to the horizontal plane and a second portion 56 having a second angle with respect to a horizontal plane, the first angle being larger than the second angle. In the embodiment shown the angled surface 40 of the actuating member 20 includes the first portion 54 having the first angle with respect to the horizontal plane and the second portion 56 having the second angle with respect to the horizontal plane. Such a dual-stage design allows the first portion to initially rapidly advance with low mechanical advantage to take up clearance between the clamp and the bedrail, and the second portion allows for secure attachment of the clamp to the bedrail with higher mechanical advantage. FIG. 6 schematically represents an embodiment of an actuating member 20 and the angled surface 40 with first and second portions 54, 56 positioned at respective first and second angles A1, A2, with respect to a horizontal plane H. Embodiments of the invention encompass a wide range of angles. In some embodiments, the first angle is greater than 45 degrees (e.g., between 50 and 75 degrees) and the second angle is 45 degrees or less. Further, more than two portions with more than two angles can be provided, including continuously varying angles. In some embodiments, the first portion is shorter in length than the second portion.

The actuating member 20 and the jaw member 25 can be made out of any suitable material. Materials that are wear-resistant with a relatively moderate coefficient of friction are particularly useful. In some embodiments, the actuating member and the jaw member include different materials (e.g., brass on steel, polymers on aluminum).

Figure 2:
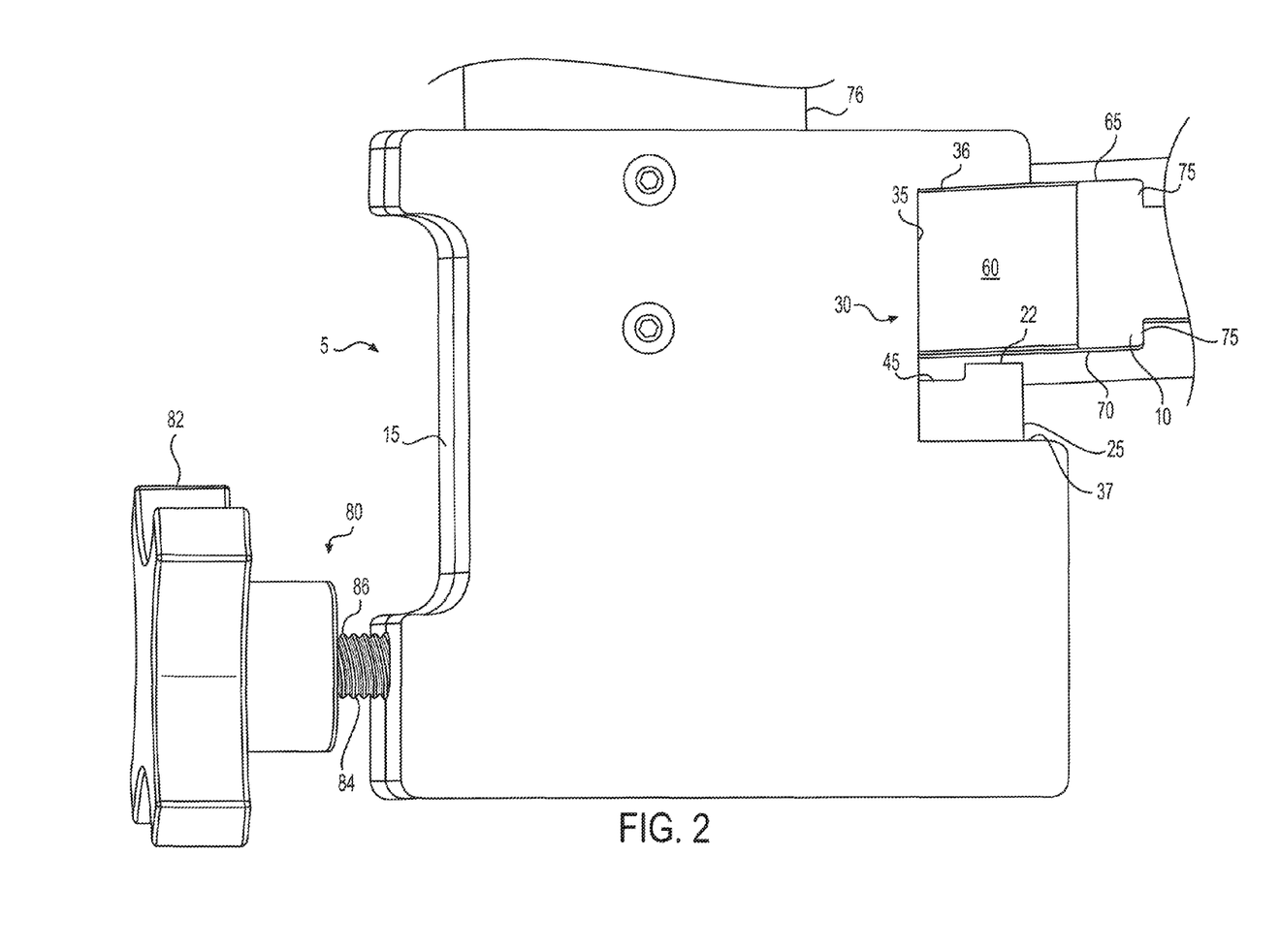
FIG. 2 is a perspective view of a bedrail clamp in accordance with an embodiment of the invention in an open position.

FIGS. 2 and 4 show the jaw member 25 in the jaw-open position. As can be seen, the jaw member 25 does not obstruct the bedrail 10 from entering or exiting the clamp housing's throat area 30. When the bedrail clamp 5 is oriented as shown in FIGS. 2 and 4, the entrance tip 22 of the jaw member 25 can be positioned close to the clamp housing's bedrail surface 37 where the bedrail 10 would enter the throat area 30. In many embodiments, in the jaw-open position, entrance tip 22 of the jaw member 25 can be spaced vertically far enough from the clamp housing's bedrail surface 36 to permit the bedrail 10 to enter the throat area 30. Two common bedrail heights are one inch and twenty-five centimeters. In some preferred embodiments, the height of the clamp housing's throat area 30 is slightly larger than those common bedrail heights. In many such embodiments, the vertical distance from bedrail surface 36 to bedrail surface 37 is slightly larger than those common bedrail heights. In some preferred embodiments, the vertical distance from the clamp housing's bedrail surface 36 to the entrance tip 22 of the jaw member 25 is slightly larger than the common bedrail heights when the jaw member 25 is in the jaw-open position.

In preferred embodiments, the jaw member 25 can move to a jaw-partially-closed position during the engagement of the rapidly-advancing, low mechanical advantage first portion 54 of the actuating member and jaw member surfaces 40/52 interface. The jaw-partially-closed position is between the jaw-open position and the jaw-closed position. In the jaw-partially-closed position, the jaw member 25 obstructs the bedrail 10, when positioned in the clamp housing's throat area 30, from exiting the clamp housing's throat area 30. The entrance tip 22 of the jaw member 25 can be brought to a position such that the vertical distance between the entrance tip 22 and bedrail surface 36 of the clamp housing 15 is less than the height of the bedrail 10. But, in the jaw-partially-closed position, the jaw member 25 of the bedrail clamp 5 does not fully engage the bedrail 10. In other words, either the clamp housing's bedrail surface 35 does not engage an outer surface 60 of the bedrail 10 or bedrail portion 50 of the jaw member 25 does not engage an inner surface 75 of the bedrail 10 (or both). The amount of space between bedrail portion 45 and lower surface 70 is how far the jaw member 25 must be translated in the closing direction to move the jaw member to the jaw-closed position. This final amount of space can be traversed and the clamp securely attached to the bedrail during the engagement of the slowly-advancing, high mechanical advantage second portion 56 of the actuating member and jaw member surfaces 40/52 interface.

FIGS. 3 and 5 show the jaw member 25 in the jaw-closed position. As can be seen, the jaw member 25 and the clamp housing 15 can engage the bedrail 10 when the bedrail 10 is positioned in the clamp housing's throat area 30. The clamp housing's bedrail surface 35 can engage a generally vertical outer surface 60 of the bedrail 10. Bedrail portion 45 of the jaw member 25 can be positioned proximate to a generally horizontal upper surface 65 or a generally horizontal lower surface 70 of the bedrail 10. In other words, the bedrail clamp 5 can be used as oriented in FIGS. 2-5, with the jaw member 25 positioned proximate to the lower surface 70 of the bedrail 10, or the bedrail clamp 5 can be turned upside down such that the jaw member 25 is positioned proximate to the upper surface 65 of the bedrail 10. Bedrail surface 36 of the clamp housing 15 can be positioned proximate to whichever of the upper or lower surfaces 65, 70 of the bedrail 10 is not positioned proximate to bedrail portion 45. In many situations, the orientation of FIGS. 2-5, with bedrail surface 36 positioned proximate to the upper surface 65 and bedrail portion 45 positioned proximate to the lower surface 70, is the preferred orientation.

In many embodiments, closing the bedrail clamp 5 involves applying force to at least the surfaces 65, 70 of the bedrail 10. As alluded to above, in preferred embodiments, bedrail portions 45, 50 of the jaw member 25 each comprise generally flat surfaces that are perpendicular to one another. In this way, bedrail portion 50 can be substantially flush with the inner surface 75 of the bedrail 10, and bedrail surface 36 of the clamp housing 15 can be substantially flush with the upper surface 65 (or lower surface 70) of the bedrail 10.

The bedrail clamp 5 of FIGS. 2-5 further includes a handle assembly 80, which can permit a user to operate the bedrail clamp 5. As shown, the handle assembly 80 includes a handle 82 and a handle shaft 84 housed by the clamp housing 15. The handle shaft 84 can have a proximal end 86 coupled to the handle 82. The handle shaft 84 can have a distal end 88 coupled to the actuating member 20. In the embodiment shown, the handle shaft is threadingly coupled to the clamp housing, such that its distal ends translates with respect to the housing as the handle is rotated.

The handle assembly 80 can take a variety of forms. In some embodiments, the handle assembly 80 is attached to the clamp housing 15 and achieves relative movement between the actuating member 20 and the clamp housing 15 by causing movement of the actuating member 20 relative to the handle assembly 80. An example of such an embodiment is shown in FIGS. 2-5, with the handle 82 comprising a knob, and the handle shaft 84 being threadingly coupled to the clamp housing. In other embodiments, the handle shaft can be threadingly coupled to the actuating member and smooth where it contacts the clamp housing. In either of such embodiments, turning the knob can cause the actuating member 20 to move between the clamp-open position and the clamp-closed position. In the embodiment shown, the knob extends horizontally from the clamp housing, which is oriented facing a user and in an ergonomic position. In other embodiments, a four-bar mechanism or a cam member on a shaft can be used to slide the actuating member.

In some embodiments, as shown in FIGS. 4-5, the clamp includes a spring 90 to bias the jaw member 25 in the jaw-open position. This can be useful to keeping the throat of the clamp open when the actuating member is in the open position. As shown, the spring 90 can include a first end 92 acting against the clamp housing 15 and a second end 94 acting against the jaw member 25. In the depicted embodiment, the second end is received within a portion of the jaw member. Also as shown, the spring can be oriented in a generally vertical position.

FIGS. 2 and 3 show a the bedrail clamp 5, with an accessory attachment support 76 that is configured to support an accessory, such as those discussed elsewhere herein. As shown, the accessory attachment support 76 includes a proximal end housed by the clamp housing 15. The accessory attachment support 76 also includes a distal end that extends away from the clamp housing 15 above the bedrail 10 when the bedrail 10 is in the clamp housing's throat area 30 and the jaw member 25 is in the jaw-closed position. In some embodiments, the accessory can be pre-attached to the bedrail clamp. In some embodiments, the accessory may be attached to the bedrail clamp after the bedrail clamp is attached to the bedrail. FIG. 4 depicts an aperture 77 configured to receive the support 76, which can optionally be secured therein by a screw 78.

In use, both the actuating member 20 and the jaw member 25 can be moved between open and closed positions. As the actuating member 20 moves in a closing direction from the clamp-open position to the clamp-closed position, the physical interfacing of the actuating member's angled surface 40 with the jaw member's surface 52 can reposition the jaw member 25 from the jaw-open position to the jaw-closed position. In some such embodiments, movement of the actuating member 20 in the closing direction repositions the jaw member 25 first from the jaw-open position to the jaw-partially-closed position and then from the jaw-partially-closed position to the jaw-closed position. In preferred embodiments, the jaw member can move to a jaw-partially-closed position during the engagement of the rapidly-advancing, low mechanical advantage first portion 54 of the actuating member and jaw member surfaces 40/52 interface, and the clamp can be securely attached to the bedrail during the engagement of the slowly-advancing, high mechanical advantage second portion 56 of the actuating member and jaw member interface.

Aspects of the present invention involve methods of attaching an accessory to a bedrail of a surgical/medical bed at a desired location without having to slide the accessory from an end of the bedrail to the desired location. A bedrail clamp, such as those discussed herein, can be provided in a surgical/medical environment. In some instances, the accessory is attached to the bedrail clamp before the bedrail clamp is attached to the bedrail. In some instances, the accessory may be attached to the bedrail clamp after the bedrail clamp is attached to the bedrail. In either case, an operator can ensure that the actuating member of the bedrail clamp is in the clamp-open position and that jaw member is in a jaw-open position. The operator can introduce the bedrail into the throat area of the bedrail clamp's clamp housing without obstruction from the jaw member.

With the bedrail in the clamp housing's throat area, the operator can close the bedrail clamp. The operator can move the actuating member in a closing direction from a clamp-open position to a clamp-closed position. In so doing, the jaw member can be repositioned from the jaw-open position to a jaw-closed position. Such repositioning of the jaw member can involve translating the jaw member in the closing direction. The jaw-closed position can involve a bedrail surface of the clamp housing engaging a surface of the bedrail.

In many preferred methods, repositioning the jaw member can involve moving the jaw member through a jaw-partially-closed position, which is between the jaw-open position and the jaw-closed position. In the jaw-partially-closed position, the jaw member can obstruct the bedrail, when positioned in the clamp housing's throat area, from exiting the clamp housing's throat area. But, in the jaw-partially-closed position, the jaw member do not fully engage the bedrail. In other words, either the clamp housing's bedrail surface does not engage the outer surface of the bedrail or the second bedrail portion of the jaw member does not engage the inner surface of the bedrail (or both). The jaw member can first be repositioned from the jaw-open position to the jaw-partially-closed position. Such repositioning can involve further translating the jaw member in the closing direction. In preferred embodiments, the operator can move the jaw member to a jaw-partially-closed position by sliding the actuating member with respect to the jaw member over the high-angle, low mechanical advantage portion of the actuating member and jaw member interface. The operator can further move the jaw member to a jaw-closed position by sliding the actuating member with respect to the jaw member over the low-angle, high mechanical advantage portion of the actuating member and jaw member interface to securely attach the clamp to the bedrail.

In the foregoing detailed description, the invention has been described with reference to specific embodiments. However, it may be appreciated that various modifications and changes can be made without departing from the scope of the invention as set forth in the appended claims. Thus, some of the features of preferred embodiments described herein are not necessarily included in preferred embodiments of the invention which are intended for alternative uses.

The invention claimed is:

1. A bedrail clamp for attaching an accessory to a bedrail of a surgical/medical bed at a desired location without having to slide the bedrail clamp from an end of the bedrail until the accessory is in the desired location, the bedrail clamp comprising:
  (a) a clamp housing that includes a throat area having a first bedrail surface and being configured to receive the bedrail;
  (b) an actuating member housed by the clamp housing and configured to move horizontally relative to the clamp housing between a clamp-open position and a clamp-closed position, the actuating member having an angled surface positioned at an angle with respect to a horizontal plane; and
  (c) a jaw member in apposition to the actuating member and housed by the clamp housing, the jaw member including
    (i) a first bedrail portion and
    (ii) a surface configured to interface physically with the actuating member's angled surface as the actuating member moves in a closing direction from the clamp-open position to the clamp-closed position to reposition the jaw member from
      (A) a jaw-open position in which the jaw member does not obstruct the bedrail from entering or exiting the clamp housing's throat area to
      (B) a jaw-closed position in which, when the bedrail is in the clamp housing's throat area, the clamp housing's first bedrail surface engages a surface of the bedrail, the jaw member's first bedrail portion engages a surface of the bedrail, wherein either the angled surface of the actuating member or the surface configured to interface physically with the actuating member's angled surface includes a first portion having a first angle with respect to the horizontal plane and a second portion having a second angle with respect to the horizontal plane, the first angle being larger than the second angle.

2. The bedrail clamp of claim 1, further including a spring to bias the jaw member in the jaw-open position.

3. The bedrail clamp of claim 1, wherein the jaw member's first bedrail portion comprises a first surface and the jaw member has a second bedrail portion with a second surface that is generally perpendicular to the first surface.

4. The bedrail clamp of claim 1, wherein clamp housing includes a vertical channel and the jaw member translates within the vertical channel.

5. The bedrail clamp of claim 1, wherein the first portion has a length and the second portion has a length, the length of the second portion being greater than the length of the first portion.

6. The bedrail clamp of claim 1, further comprising a handle assembly, which includes a handle and a handle shaft housed by the clamp housing, the handle shaft having a proximal end coupled to the handle and a distal end coupled to the actuating member.

7. The bedrail clamp of claim 6, wherein the handle shaft is threadingly coupled to the clamp housing.

8. The bedrail clamp of claim 6, wherein the handle comprises a knob and the distal end of the handle shaft is threadingly coupled to the actuating member such that turning the knob causes the actuating member to move between the clamp-open position and the clamp-closed position.

9. The bedrail clamp of claim 1, wherein the first angle is more than forty-five degrees and the second angle is forty-five degrees or less.

10. The bedrail clamp of claim 1, wherein the angled surface of the actuating member includes the first portion having the first angle with respect to the horizontal plane and the second portion having the second angle with respect to the horizontal plane.

11. The bedrail clamp of claim 1, wherein the actuating member moves horizontally in a horizontal channel defined by the clamp housing.

12. The bedrail clamp of claim 1, further comprising an accessory attachment support having a proximal end housed by the clamp housing and a distal end that extends away from the clamp housing above the bedrail when the bedrail is in the clamp housing's throat area and the jaw member is in the jaw-closed position, the accessory attachment support being configured to support the accessory.

13. A method of attaching an accessory to a bedrail of a surgical/medical bed at a desired location without having to slide the accessory from an end of the bedrail to the desired location, the method comprising:
(a) providing a bedrail clamp that includes:
(i) a clamp housing comprising a throat area that includes a first bedrail surface and that is configured to receive the bedrail,
(ii) an actuating member housed by the clamp housing and configured to move relative to the clamp housing between a clamp-open position and a clamp-closed position, the actuating member having an angled surface positioned at an angle with respect to a horizontal plane, and
(iii) a jaw member housed by the clamp housing, the jaw member comprising first and second bedrail portions, the jaw member including a surface configured to interface physically with the actuating member's angled surface, wherein either the angled surface of the actuating member or the surface configured to interface physically with the actuating member's angled surface includes a first portion having a first angle with respect to the horizontal plane and a second portion having a second angle with respect to the horizontal plane, the first angle being larger than the second angle;
(b) introducing the bedrail into the clamp housing's throat area without obstruction from the jaw member; and
(c) moving the actuating member in a closing direction from the clamp-open position to jaw-partially-closed position between the clamp-open position and the clamp-closed position by sliding the actuating member with respect to the jaw member over the first portion and further moving the jaw member to the clamp closed position by sliding the actuating member with respect to the jaw member over the second portion to securely attach the clamp to the bedrail.

14. The method of claim 13, wherein the angled surface of the actuating member includes the first portion having the first angle with respect to the horizontal plane and the second portion having the second angle with respect to the horizontal plane.

15. The method of claim 13, wherein clamp housing includes a vertical channel and the jaw member translates within the vertical channel.

16. The method of claim 13, wherein the actuating member moves horizontally in a horizontal channel defined by the clamp housing.

17. The method of claim 13, further comprising rotating a handle assembly to move the actuating member, the handle assembly including a handle and a handle shaft housed by the clamp housing, the handle shaft having a proximal end coupled to the handle and a distal end coupled to the actuating member.

18. The method of claim 13, wherein the first portion has a length and the second portion has a length, the length of the second portion being greater than the length of the first portion.

* * * * *